United States Patent
Park et al.

(10) Patent No.: US 7,027,867 B2
(45) Date of Patent: Apr. 11, 2006

(54) IMPLANTABLE CARDIAC DEVICE HAVING A SYSTEM FOR DETECTING T WAVE ALTERNAN PATTERNS AND METHOD

(75) Inventors: Euljoon Park, Stevenson Ranch, CA (US); Kerry Bradley, Glendale, CA (US)

(73) Assignee: Pacesetter, Inc., Sylmar, CA (US)

( * ) Notice: Subject to any disclaimer, the term of this patent is extended or adjusted under 35 U.S.C. 154(b) by 699 days.

(21) Appl. No.: 10/186,069

(22) Filed: Jun. 28, 2002

(65) Prior Publication Data

US 2004/0002743 A1  Jan. 1, 2004

(51) Int. Cl.
*A61N 1/18* (2006.01)

(52) U.S. Cl. .......................... 607/25; 600/517
(58) Field of Classification Search .............. 607/25, 607/26; 600/508, 509, 517
See application file for complete search history.

(56) References Cited

U.S. PATENT DOCUMENTS

| | | | |
|---|---|---|---|
| 4,556,062 A * | 12/1985 | Grassi et al. ................. 607/26 |
| 4,802,491 A | 2/1989 | Cohen et al. ................ 128/702 |
| 5,148,812 A | 9/1992 | Verrier et al. ............... 128/704 |
| 5,197,480 A * | 3/1993 | Gebhardt .................... 600/510 |
| 5,265,617 A | 11/1993 | Verrier et al. ............... 128/704 |
| 5,300,092 A * | 4/1994 | Schaldach ................... 607/18 |
| 5,466,254 A | 11/1995 | Helland ...................... 607/123 |
| 5,476,483 A | 12/1995 | Bornzin et al. ............... 607/17 |
| 5,547,285 A | 8/1996 | Hutzel et al. ................. 384/15 |
| 5,549,650 A * | 8/1996 | Bornzin et al. ............... 607/24 |
| 5,560,370 A | 10/1996 | Verrier et al. ............... 128/705 |
| 5,842,997 A | 12/1998 | Verrier et al. ............... 600/518 |
| 5,921,940 A * | 7/1999 | Verrier et al. ............... 600/518 |
| 6,016,443 A * | 1/2000 | Ekwall et al. ............... 600/519 |
| 6,169,919 B1 * | 1/2001 | Nearing et al. ............. 600/518 |
| 6,493,586 B1 * | 12/2002 | Stahmann et al. ............ 607/27 |
| 6,823,213 B1 * | 11/2004 | Norris et al. .................. 607/9 |
| 2001/0007948 A1 * | 7/2001 | Stoop et al. .................. 607/14 |
| 2003/0060854 A1 * | 3/2003 | Zhu ............................ 607/25 |

* cited by examiner

*Primary Examiner*—George R. Evanisko
*Assistant Examiner*—Fernando Aguel

(57) ABSTRACT

A system and method for use in an implantable cardiac device that delivers electrical therapy to a patient's heart determines if a T wave alternan pattern of the patient's heart exists. The system includes a sensing circuit that generates an electrical signal representing electrical activity of the patient's heart. A morphology detector measures a magnitude of a T wave characteristic of each T wave in the electrical signal of a predetermined number of cardiac cycles of the heart. A discriminator then determines, responsive to the measured T wave characteristic magnitudes, if a T wave alternan pattern exists. A T wave alternan pattern may be determined to exist if the number of measured T wave characteristic magnitudes greater than and less than a T wave characteristic magnitude baseline are substantially equal and each greater than a given number.

51 Claims, 5 Drawing Sheets

IMPLANTABLE CARDIAC DEVICE HAVING A SYSTEM FOR DETECTING T WAVE ALTERNAN PATTERNS AND METHOD

FIELD OF THE INVENTION

The present invention generally relates to an implantable cardiac device that delivers electrical therapy to a patient's heart. The present invention more particularly relates to a system for use in such a device for detecting T wave alternan patterns.

BACKGROUND OF THE INVENTION

Implantable cardiac stimulation devices are well known in the art. They include implantable pacemakers which provide stimulation pulses to a heart to cause a heart, which would normally or otherwise beat too slowly or at an irregular rate, to beat at a controlled normal rate. They also include defibrillators which detect when the atria and/or the ventricles of the heart are in fibrillation and apply cardioverting or defibrillating electrical energy to the heart to restore the heart to a normal rhythm. Implantable cardiac stimulation devices may also include the combined functionalities of a pacemaker and a defibrillator.

As is well known, implantable cardiac stimulation devices sense cardiac activity for monitoring the cardiac condition of the patient in which the device is implanted. By sensing the cardiac activity of the patient, the device is able to provide cardiac stimulation therapy when it is required.

As is well known, a cardiac cycle on an electrocardiogram (ECG) extends from one heart beat (QRS complex) to the next. During each cardiac cycle, a T wave occurs. The T wave is a low-frequency wave that follows the ST-segment and represents repolarization of the ventricular myocardium. Alternate occurring T waves (odd and even) are referred to as T wave alternans.

T wave alternan patterns are known to be a precursor for sudden cardiac death. In the past, detection of T wave alternan patterns has been performed using surface ECGs. Implementation of such detection has included the measurement, on a beat-to-beat basis, of the micro-volt level changes in the T wave amplitude from the surface ECG. Then, the long record of time series of T wave amplitude change is transformed into the frequency domain by fourier series transformation (FFT). A prominent peak in the FFT at 0.5 Hz would verify the existence of a T wave alternan pattern.

Unfortunately, the above detection method requires the use of medical equipment that must be operated by medical personnel in a medical facility such as a physician's office. The detection requires long term recording of surface ECGs and off-line analysis with robust computation equipment. As a result, T wave alternan pattern monitoring has been inconvenient and cumbersome. As a result, it is difficult to provide continuous and regular T wave alternan pattern monitoring.

Many patients who would benefit from T wave alternan pattern monitoring have an implanted cardiac device such as an implantable defibrillator or a combined defibrillator pacemaker. It would thus be highly desirable if such an implanted device could detect for T wave alternan patterns. However, the prior art detection method does not lend itself for such application due to, for example, the required long term monitoring, surface ECG, and robust computational requirements for fourier series transformation.

In order for an implanted cardiac device to provide T wave alternan pattern monitoring, there is a need for a new and different approach. The present invention addresses that need.

SUMMARY OF THE INVENTION

The present invention provides a system for use in an implantable cardiac device that delivers electrical therapy to a patient's heart for detecting a T wave alternan pattern of the patient's heart. The system includes a sensing circuit that generates an electrical signal representing electrical activity of the patient's heart. The system further includes a morphology detector that measures a magnitude of a T wave characteristic of each T wave in the electrical signal of a predetermined number of cardiac cycles of the heart and a discriminator that determines, responsive to the measured T wave characteristic magnitudes, if a T wave alternan pattern is present.

In detecting the presence of a T wave alternan pattern, the discriminate determines if a number of measured T wave characteristic magnitudes greater than and less than a T wave characteristic magnitude baseline are substantially equal and each greater than a given number. The T wave characteristic baseline may be an average of the measured T wave characteristic magnitudes or a mean of the measured T wave characteristic magnitudes.

The T wave characteristic may be T wave amplitude, T wave slope or T wave area.

If the implantable cardiac device includes a pulse generator that provides pacing pulses to the patient's heart during paced cardiac cycles, the morphology detector preferably measures the magnitude of the T wave characteristic of only T waves occurring during paced cardiac cycles or occurring during unpaced cardiac cycles. Preferably, the measured cardiac cycles are consecutive cardiac cycles.

The system may further include a timer that activates the detection at spaced apart times. Alternatively, or in addition, the system may further include an activity detector that detects when the patient is at rest and which enables the detection only when the patient is at rest.

The implantable cardiac device preferably includes a lead system, coupled to the sensing circuit, having a plurality of T wave sensing electrode configurations. The system in turn includes a selecting circuit that selects an electrode configuration from the plurality of T wave sensing electrode configurations that maximizes the measured T wave characteristic.

To report detection outcomes, the system may further include a telemetry circuit that transmits to an external receiver the presence of a detected T wave alternan pattern. In addition or alternatively, the system may further include a patient alert that provides an indication, perceptible by the patient, of a detected T wave alternan pattern. For each T wave alternan detection, the system may further determine and store in internal memory for later transmission to an external receiver, at least one of heart rate, time of T wave alternan pattern detection, patient activity level, and T wave characteristic histogram data for the T wave alternan pattern detection.

In view of the above, the present invention further provides a method, for implementation in an implantable cardiac device that delivers electrical therapy to a patient's heart, of detecting a T wave alternan pattern of the patient's heart. The method includes the steps of generating an electrical signal representing electrical activity of the patient's heart, measuring a magnitude of a T wave characteristic of each T wave in the electrical signal of a predetermined number of cardiac cycles of the heart, and responsive to the measured T wave characteristic magnitudes, detecting a T wave alternan pattern.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
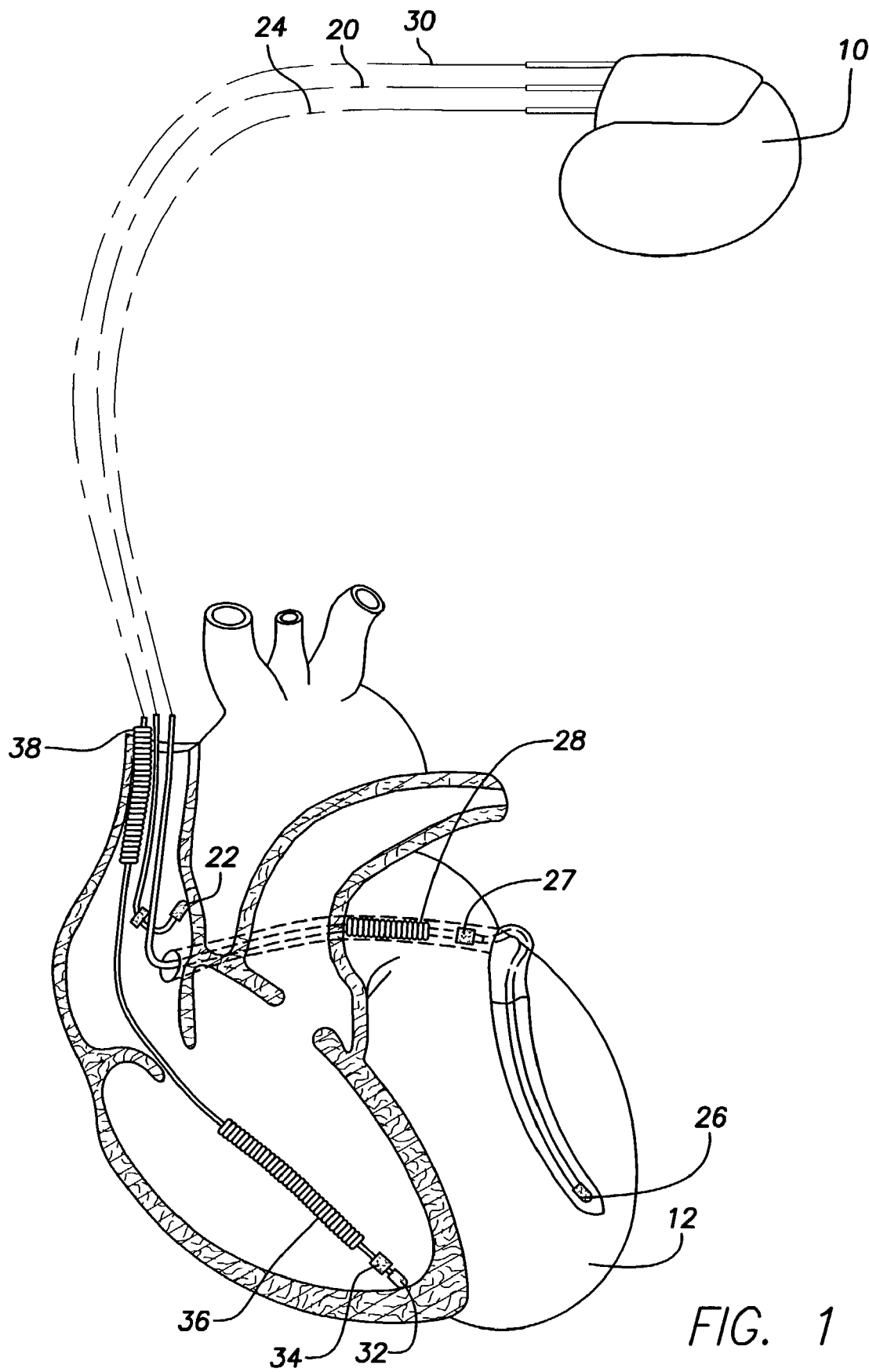
FIG. 1 is a simplified diagram illustrating an implantable stimulation device embodying the system of the present invention in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. patent application Ser. No. 09/457,277, filed Dec. 8, 1999, entitled "A Self-Anchoring, Steerable Coronary Sinus Lead" (Pianca et al); and U.S. Pat. No. 5,466,254, "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
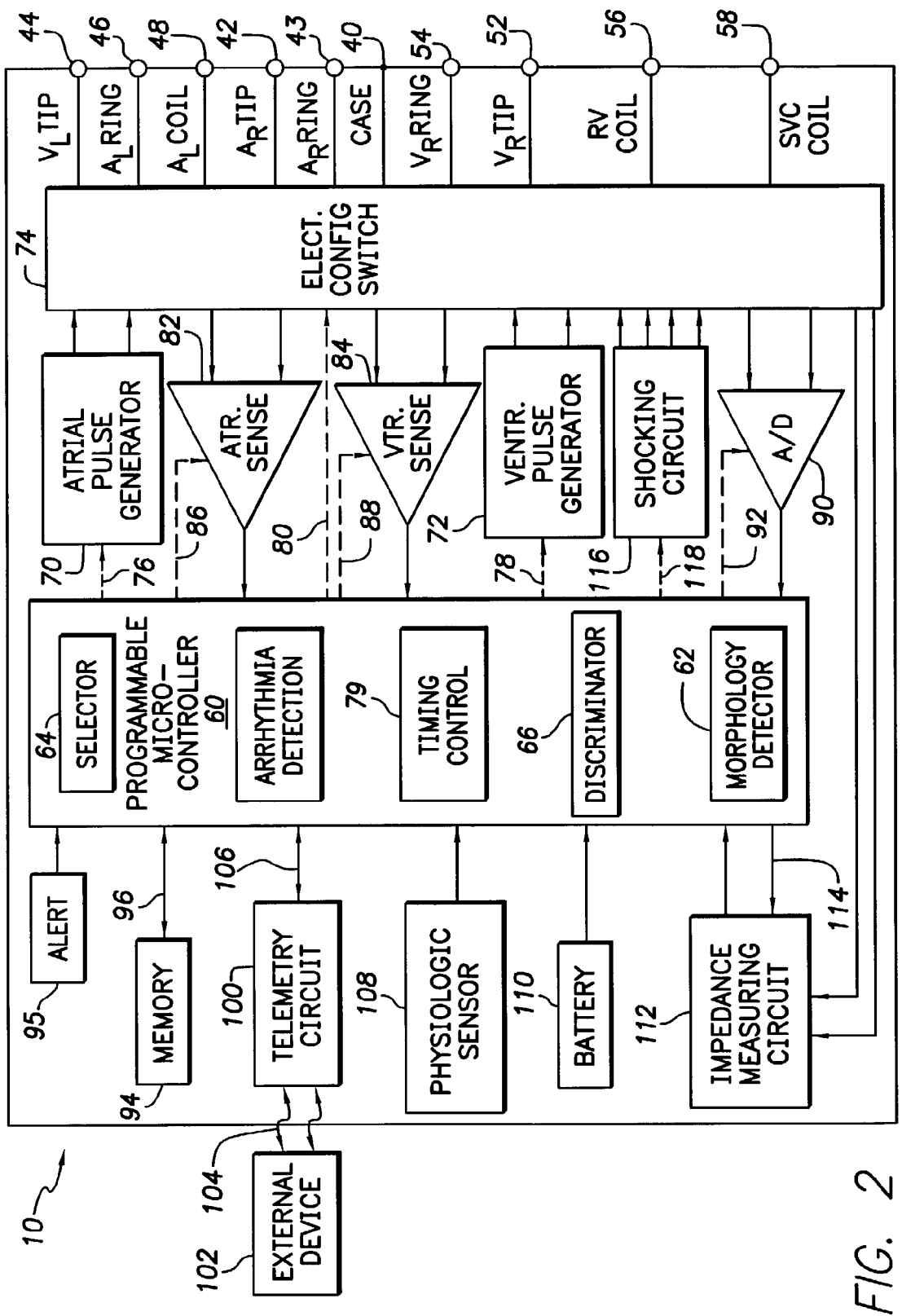
FIG. 2 is a functional block diagram of the device of FIG. 1 illustrating the basic elements thereof which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. In accordance with the present invention, the timing control 79 may also be employed to time spaced apart times for activating T wave alternan pattern detection.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes. Advantageously, the data acquisition system 90 may be utilized in acquiring data for T wave alternan pattern detection in accordance with the present invention as more particularly described subsequently with respect to the data acquisition subroutine of FIG. 4.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. The memory 94 may further be used to store data associated with T wave alternan pattern detection in accordance with the present invention. That data may include, for example, heart rate, time of T wave alternan pattern detection, and patient activity level for the T wave alternan pattern detection.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses. While shown as being included within the stimulation device 10, it is to be understood that the physiologic sensor 108 may also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc. However, any sensor may be used which is capable of sensing a physiological parameter which corresponds to the exercise state of the patient.

In this embodiment of the present invention, the physiologic sensor 108 includes a rest state and active state sensor that can detect rest and active states. One such sensor compares short term activity average to long term activity average to determine if the patient is active or inactive and also uses "activity variance" to detect a low variance in the measurement corresponding to the rest state. For a complete description of the above activity sensor, see U.S. Pat. No. 5,476,483 (Bornzin, et al.), issued Dec. 19, 1995, which patent is hereby incorporated by reference.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Now that the device 10 has been generally described, those elements and features of the device which more particularly pertain to this embodiment will now be described. During data acquisition of the T wave alternan pattern detection, a predetermined T wave characteristic magnitude of each T wave of a given number of cardiac cycles is measured. The predetermined T wave characteristic may be, for example, T wave amplitude, T wave slope, or T wave area in the electrogram signal generated by the sensing circuits of the data acquisition system 90. This requires the data acquisition system 90 to include a sensing circuit having a sensitivity in the range of 0.3 mV to 10 mV for example.

Further, the lead system of FIG. 1 offers a plurality of different T wave sensing electrode configurations. Those configurations include, for example, the left ventricular tip electrode 26 with either the right ventricular tip electrode 32 or the right ventricular ring electrode 34. Other possible electrode configurations include the case 40 and either the right ventricular tip electrode 32 or the right ventricular ring electrode 34 or the right ventricular coil electrode 36 and the left ventricular tip electrode 26. Here, the switch 74 may be used to advantage in permitting the selection, by a selector 64 of the microcontroller 60, of the T wave sensing electrode configuration that maximize the magnitude of the predetermined T wave characteristic to be measured.

For measuring the T wave characteristic, the microcontroller includes a morphology detector 62. When the predetermined T wave characteristic is T wave amplitude, the morphology detector 62 may be used to measure the T wave amplitudes. When the predetermined T wave characteristic is T wave slope, the morphology detector may be used to measure the slope of the T wave in the electrogram signal generated by the acquisition system 90. Similarly, if the predetermined T wave characteristic is T wave area, the morphology detector may be used to calculate the area under the T wave in the electrogram signal.

To perform data analysis of the measured T wave characteristics, the microcontroller includes a discriminator 66. As will be seen hereinafter, the data analysis requires the calculation of a T wave characteristic baseline and comparisons of each measured T wave characteristic magnitude to the baseline. These functions may be performed by the discriminator 66 along with other functions to be described subsequently in connection with the flow charts of FIGS. 3–5.

To report the results of a T wave alternan pattern detection, the telemetry circuit 100 may be employed. After each detection, the presence or absence of a detected T wave alternan pattern may be stored in memory 94 along with other information associated with the detection. As previously mentioned, the associated data may include heart rate, the time of the detection, and the activity level of the patient. The memory 94 may further include two histograms, one histogram for the T wave amplitudes when there is no detected T wave alternan pattern and the other for the T wave amplitudes when there is a detected T wave alternan pattern. The histograms enable the physician to see the distribution of the T wave amplitudes. Once stored in memory 94, the data is available for transmission by telemetry circuit 100 to an external receiver 102 for display at follow-up, for example.

The device 10 further includes an alert 95. The alert may be activated when one or more T wave alternan patterns are detected. The alert may take the form of any device capable of providing an output or indication perceptible by the patient. To this end, the alert 95 may be a speaker or a vibrator, for example.

Figure 3:
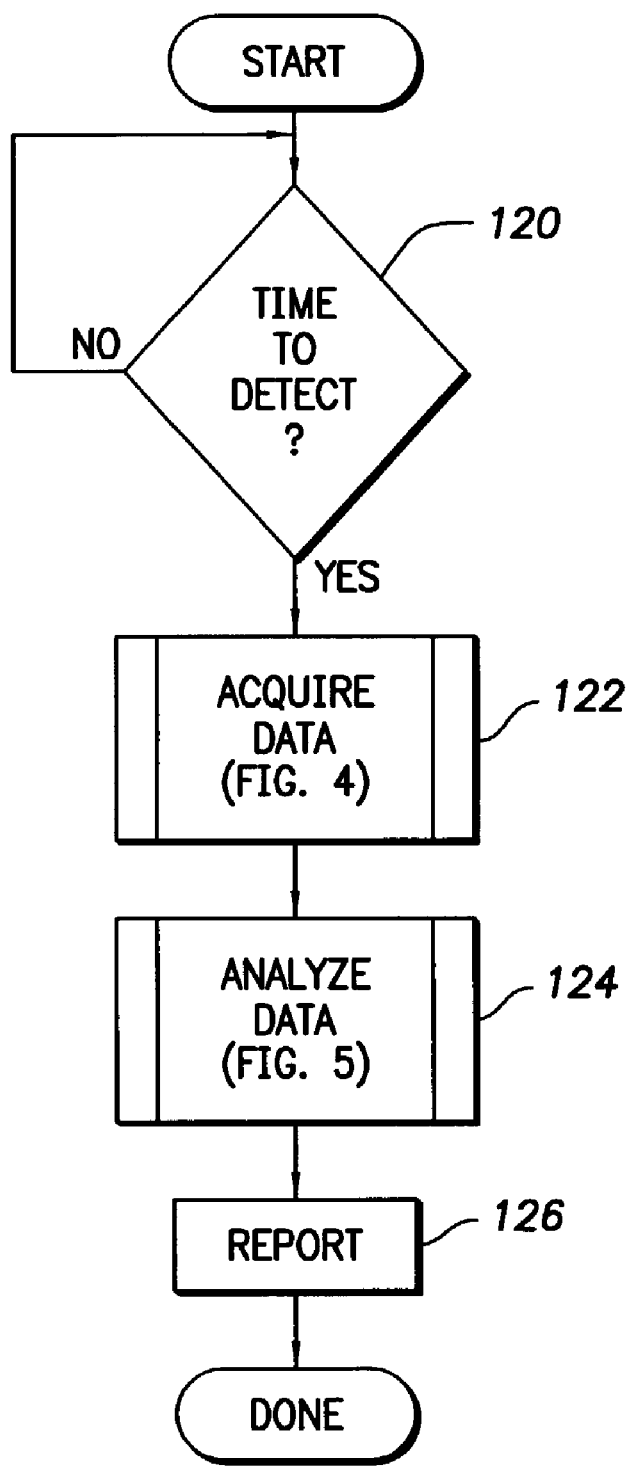
FIG. 3 is a flow chart describing an overview of the operation of one embodiment of the present invention.

In FIG. 3, a flow chart is shown describing an overview of the operation and novel features implemented in one embodiment of the device 10. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The T wave alternan pattern detection in accordance with this embodiment of the present invention initiates in FIG. 3 at decision block 120. Here, the microcontroller 60 determines if it is time to initiates a T wave alternan pattern detection. The time to detect may be one of the spaced apart times timed by the timing control 79 as previously described. Alternatively, or in addition, the time to detect may be further conditioned on the patient being at rest as determined by the physiology sensor 108 and having a stable heart rate while at rest. If it is not time to initiate the T wave alternan pattern detection, the process returns. However, if it is time to detect for a T wave alternan pattern, the process then advances to a subroutine block 122 for acquiring data. As will be seen hereinafter with respect to FIG. 4, the data acquisition includes the measurement of a T wave characteristic magnitude for each T wave occurring during a consecutive number of cardiac cycles. Preferably, all of the consecutive cardiac cycles are either paced cardiac cycles or unpaced (intrinsic) cardiac cycles. As previously mentioned, the predetermined T wave characteristic to be measured may be T wave amplitude, T wave area, or T wave slope in the electrogram signal provided by the data acquisition system 90 (FIG. 2).

Once the required data has been acquired, the process advances to a further subroutine block 124 wherein the data is analyzed. As will be seen hereinafter with respect to FIG. 5, the data analysis first proceeds with the calculation of a T wave characteristic baseline. The baseline may be the average of each of the T wave characteristic measurements made during the subroutine 122 or it could be a mean value.

Once the baseline is determined, it is then determined if each individual T wave measurement is substantially equal to the baseline, less than the baseline, or greater than the baseline. The results are then sorted by incrementing counters corresponding to each comparison.

Following the comparison of each measured T wave characteristic magnitude with the baseline and the incrementing of the counters, it is then determined if a T wave alternan pattern exists. In accordance with the present invention, a T wave alternan pattern exists if the number of measured T wave characteristic magnitudes greater than and less than the T wave characteristic magnitude baseline are substantially equal and each greater than a given number. For example, if 32 consecutive T wave characteristics are measured, a T wave alternan pattern may be determined to exist if the number of T wave magnitudes greater than the baseline is substantially equal to the number of measured T wave magnitude less than the baseline and if their sum is greater than half of all of the measured T wave characteristic magnitudes, for example, greater than 16. In other words, the number of T wave characteristic magnitudes greater than the baseline and the number of T wave characteristic magnitudes less than the baseline each should be greater than $\frac{1}{4}^{th}$ of 32 or eight, and be substantially equal to each other.

The data analysis subroutine 124 as will be seen hereinafter concludes with the recording of the results of the T wave alternan pattern detection. First, a record is made in the memory 94 as to the existence or nonexistence of a T wave alternan pattern. Also, during the detection process, the patient's heart rate may be determined and stored in memory as associated data. Still further, the time of the T wave alternan pattern detection may be recorded along with the activity level of the patient. Lastly, the T wave amplitudes are loaded into one of the previously mentioned histograms.

Once the data analysis subroutine 124 is complete, the process then advances to an activity block 126 wherein the recorded results are reported. The activity block 126 may be implemented by a physician interrogating the implanted device using the telemetry circuit at which point the telemetry circuit 100 transmits to a non-implanted receiver the results of the various T wave alternan pattern detections. In addition, should a T wave alternan pattern be detected, the report activity block 126 contemplates also providing the patient with a perceptible indication of the positive detection. This report or alert may be performed using the alert circuit 95 (FIG. 2) which may include an acoustical device for creating a vibration or a sound perceptible to the patient. Upon perceiving the indication of a positive detection of a T wave alternan pattern, the patient may then alert his physician of the positive detection. Once the report activity block 126 has completed, the process completes.

Figure 4:
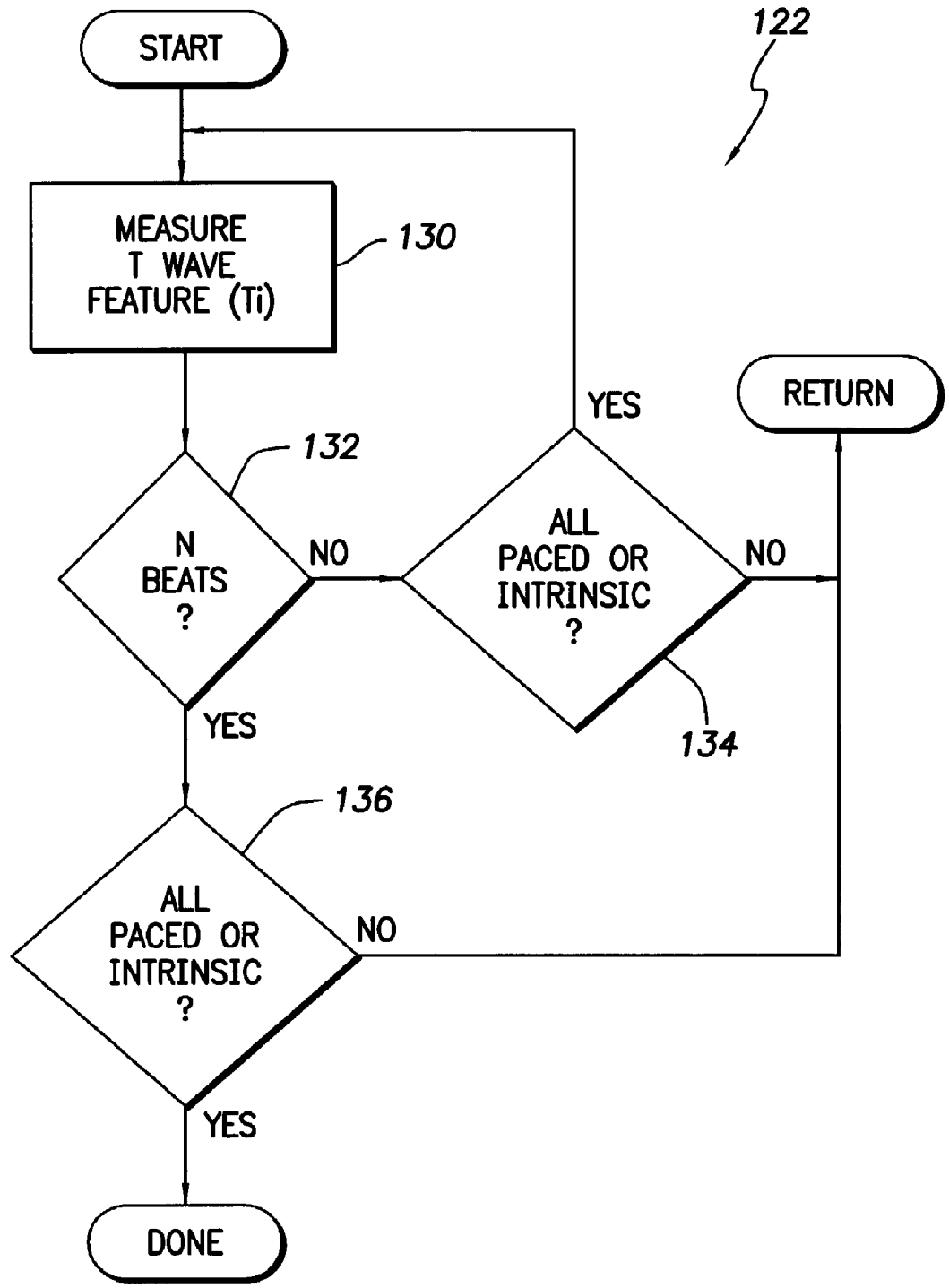
FIG. 4 is a flow diagram describing the data acquisition subroutine of FIG. 3.

FIG. 4 more particularly describes the data acquisition subroutine 122 of FIG. 3. The subroutine 122 initiates at an activity block 130 where the predetermined T wave characteristic or feature magnitude is measured for a first T wave. Following activity block 130, the subroutine then advances to a decision block 132 where it is determined if the T wave characteristic magnitude has been measured for all of the given number of N beats. If not all of the T wave characteristic magnitudes have been measured, the process then advances to decision block 134 wherein it is determined if all of the T wave characteristic or feature magnitudes which have been measured were measured for all paced or all intrinsic cardiac cycles. If not, the subroutine then returns. However, if all of the measured T wave characteristic magnitudes correspond to T waves of all paced or all intrinsic cardiac cycles, the process then returns to activity block 130 for measuring the T wave characteristic magnitude of the next T wave.

If, in decision block 132, it is determined that the T wave characteristic magnitudes for the T waves occurring in all N cardiac cycles have been measured, the process then advances to decision block 136 wherein it is determined if all of the T wave measurements were for paced or intrinsic cardiac cycles. If not all of the cardiac cycles were paced or intrinsic cardiac cycles, the process returns. However, if all of the consecutive cardiac cycles were paced or intrinsic cardiac cycles, then the data acquisition subroutine is completed and the overall process then advances to the next subroutine block 124 for data analysis as shown in FIG. 3.

Figure 5:
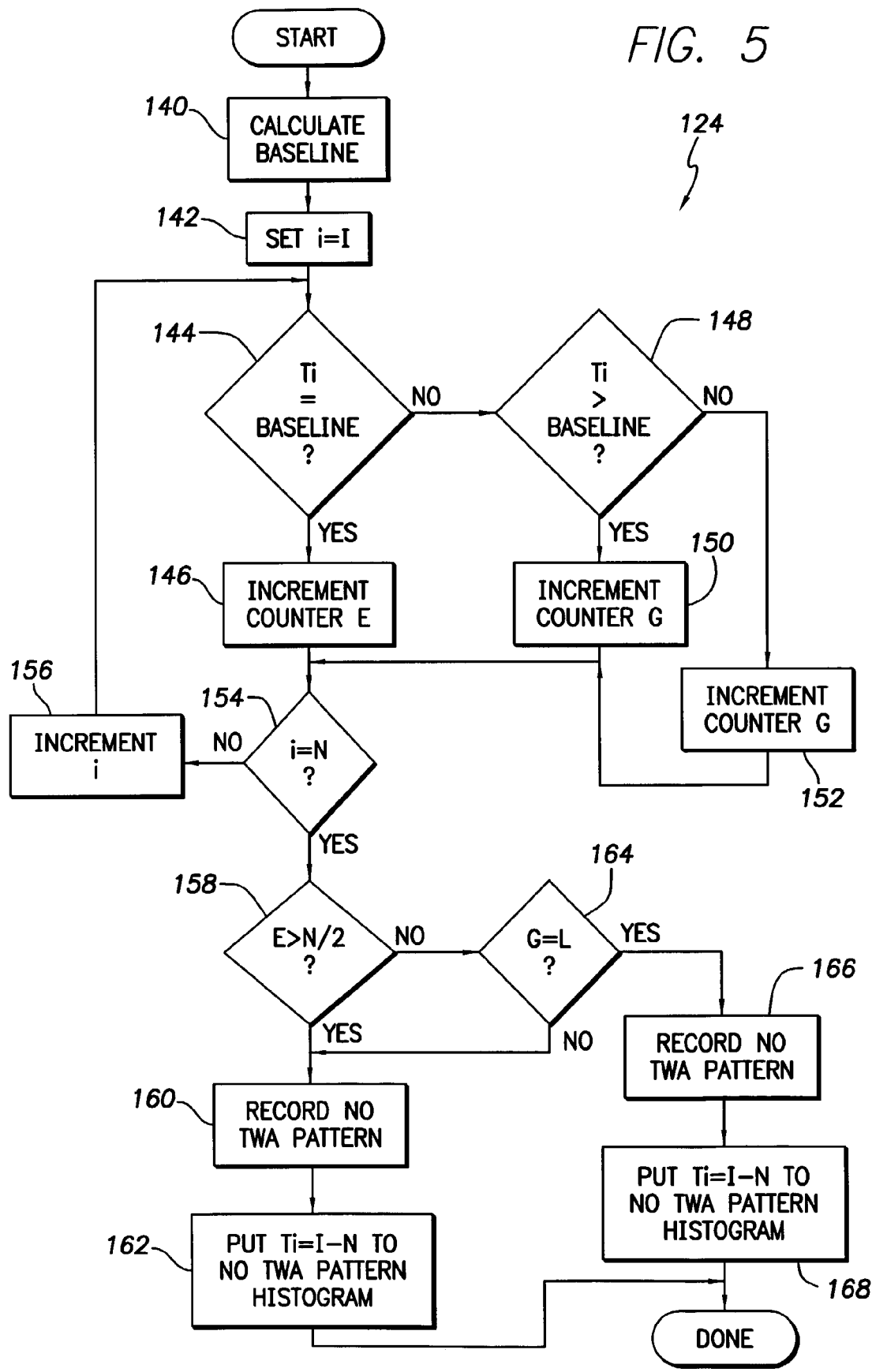
FIG. 5 is a flow diagram describing the data analysis subroutine of FIG. 3.

FIG. 5 more particularly describes the data analysis subroutine 124 of FIG. 3. The subroutine 124 initiates at an activity block 140 wherein the T wave characteristic magnitude baseline is determined. As previously mentioned, the baseline may be the average or the mean of all of the T wave characteristic magnitude measurements. Once the baseline is calculated in accordance with activity block 140, the process advances to activity block 142 whereat i is set equal to one. This indicates that the first T wave characteristic magnitude measured will now be compared to the baseline calculated in activity block 140. To that end, the process advances to decision block 144. In decision block 144 it is determined if the first T wave characteristic magnitude measured is substantially equal to the baseline. If it is, the process immediately advances to activity block 146 wherein a counter E is incremented. Counter E maintains the count of the number of measured T wave characteristic magnitudes which are substantially equal to the baseline.

If the first measured T wave characteristic magnitude is not substantially equal to the baseline, the process then advances to decision block 148 wherein it is determined if the first measured T wave characteristic magnitude is greater than the baseline. If it is, the process advances to activity block 150 wherein a counter G is incremented. Counter G maintains the count of the number of measured T wave characteristic magnitudes which are greater than the baseline.

If the first measured T wave characteristic magnitude is not greater than the baseline, it must then be less than the baseline and the process advances to activity block 152 wherein a counter L is incremented. Counter L maintains the count of the number of measured T wave characteristic magnitudes which are less than the baseline.

Following any one of activity blocks 146, 150, and 152, the process then advances to decision block 154 wherein it is determined if all of the measured T wave characteristic magnitudes have been sorted with respect to the baseline. If not all have been sorted, then the process advances to activity block 156 wherein i is incremented and the process returns to decision block 144 to sort the next measured T wave characteristic magnitude.

When all of the measured T wave characteristic magnitudes have been sorted, the process advances from decision block 154 to decision block 158. In decision block 158, it is determined if the count in counter E, representing the number of measured T wave characteristic magnitude substantially equal to the baseline, is greater than ½ of the total number of measured T wave characteristic magnitudes. If the number of measured T wave characteristic magnitude substantially equal to the baseline is greater than ½ of the total number of measured T wave characteristic magnitudes, the process advances to activity block 160 wherein it is recorded that no T wave alternan pattern exists for this detection. The process then advances to activity block 162 wherein the T wave amplitudes are loaded into the no T wave alternan pattern histogram.

If the number of measured T wave characteristic magnitudes is less than ½ of the total number of measured T wave characteristic magnitudes, the process advances from decision block 158 to decision block 164 to determine if the number of counts in counter G is substantially equal to the number of counts in counter L. In other words, in decision block 164, it is determined if the number of measured T wave characteristic magnitudes greater than the baseline is substantially equal to the number of measured T wave characteristic magnitudes less than the baseline. If the number of T wave characteristic magnitudes greater than the baseline is not substantially equal to the number of measured T wave characteristic magnitudes less than the baseline, the process then advances to activity block 160 where again a record is made that no T wave alternan pattern exists for this detection. However, if the number of measured T wave characteristic magnitudes greater than the baseline is substantially equal to the number of measured T wave characteristic magnitudes less than the baseline, the process then advances to activity block 166 wherein it is recorded that a T wave alternan pattern does exists. The process then advances to activity block 168 wherein the T wave amplitudes are loaded into the T wave alternan pattern histogram.

Once the histogram data is loaded in accordance with activity block 162 or activity block 168, the T wave amplitude distributions are then available for use by the physician at the patient's next follow-up visit. The overall process then advances to activity block 126 of FIG. 3 for reporting the results of the T wave alternan pattern detection.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. In an implantable cardiac device, a system for detecting a T wave alternan pattern of a patient's heart, comprising:
    a sensing circuit that generates an electrical signal representing electrical activity of the patient's heart;
    morphology detector that receives the electrical signal from the sensing circuit and that measures a metric of a characteristic for each T wave in the electrical signal; and
    a discriminator that receives the measured T wave characteristic metrics from the morphology detector and that determines, responsive to the measured T wave characteristic metrics for a plurality of T waves, if a T wave alternan pattern is present;
    wherein the discriminator determines if a number of measured T wave characteristic magnitudes greater than and less than a T wave characteristic magnitude baseline are substantially equal and each greater than a given number.

2. The system of claim 2 wherein the T wave characteristic baseline is an average of the measured T wave characteristic magnitudes and wherein the system includes a processor that averages the measured T wave characteristic magnitudes.

3. The system of claim 1 wherein the T wave characteristic baseline is a mean of the measured T wave characteristic magnitudes and wherein the system includes a processor that determines the mean.

4. The system of claim 1 wherein the given number is one-fourth of the predetermined number.

5. The system of claim 1 further comprising a timer that activates the sensing circuit at spaced apart times.

6. The system of claim 1 further comprising an activity detector that detects when the patient is at rest and wherein the sensing circuit is activated by the activity detector when the patent is at rest.

7. The system of claim 1 wherein the T wave characteristic is T wave amplitude and wherein the morphology detector measures T wave amplitude magnitude of each T wave of the predetermined number of cardiac cycles.

8. The system of claim 1 wherein the implantable cardiac device includes a pulse generator that provides pacing pulses to the patient's heart during paced cardiac cycles and wherein the morphology detector measures the magnitude of the T wave characteristic of only T waves occurring during paced cardiac cycles.

9. The system of claim 1 wherein the morphology detector measures the magnitude of the T wave characteristic of only intrinsic T waves.

10. The system of claim 1 wherein the predetermined number of cardiac cycles are consecutive cardiac cycles.

11. The system of claim 1 wherein the T wave characteristic is a T wave slope and wherein the morphology detector measures a T wave slope magnitude of each T wave of the predetermined number of cardiac cycles.

12. The system of claim 1 wherein the T wave characteristic is T wave area and wherein the morphology detector measures T wave area magnitude of each T wave of the predetermined number of cardiac cycles.

13. The system of claim 1 wherein the implantable cardiac device includes a lead system coupled to the sensing circuit, the lead system having a plurality of T wave sensing electrode configurations, and wherein the system includes a selecting circuit that selects an electrode configuration from the plurality of T wave sensing electrode configurations that maximizes the measured T wave characteristic.

14. The system of claim 1 further comprising a telemetry circuit that transmits to an external receiver the presence of a detected T wave alternan pattern.

15. The system of claim 1 further comprising a patient alert that provides an indication, perceptible by the patient, of a detected T wave alternan pattern.

16. The system of claim 1 further comprising a memory for storing at least one of heart rate, time of T wave alternan pattern detection, and patient activity level for the T wave alternan pattern detection.

17. The system of claim 1 further comprising a memory for maintaining a histogram of the T wave characteristic magnitudes.

18. In an implantable cardiac device that delivers electrical therapy to a patient's heart, a system for detecting a T wave alternan pattern of the patients heart, comprising:
   sensing means for generating an electrical signal representing electrical activity of the patients heart;
   measuring means for measuring a magnitude of a T wave characteristic for each T wave in the electrical signal; and
   detecting means, responsive to the measured T wave characteristic magnitudes for a plurality of T waves, for detecting a T wave alternan pattern;
   wherein the detecting means includes means for determining if a number of measured T wave characteristic magnitudes greater than and less than a T wave characteristic magnitude baseline are substantially equal and each greater than a given number.

19. The system of claim 18 wherein the T wave characteristic baseline is an average of the measured T wave characteristic magnitudes and wherein the system includes processing means for averaging the measured T wave characteristic magnitudes.

20. The system of claim 18 wherein the T wave characteristic baseline is a mean of the measured T wave characteristic magnitudes and wherein the system includes processing means for calculating the mean.

21. The system of claim 18 wherein the given number is one-fourth of the predetermined number.

22. The system of claim 18 further comprising timing means for activating the sensing circuit at spaced apart times.

23. The system of claim 18 further comprising activity detecting means for detecting when the patient is at rest and wherein the sensing means generates the electrical signal when the patient is at rest.

24. The system of claim 18 wherein the T wave characteristic is T wave amplitude and wherein the measuring means includes means for measuring T wave amplitude magnitude of each T wave of the predetermined number of cardiac cycles.

25. The system of claim 18 wherein the implantable cardiac device includes pacing means for providing pacing pulses to the patient's heart during paced cardiac cycles and wherein the measuring means measures the magnitude of the T wave characteristic of only T waves occurring during paced cardiac cycles.

26. The system of claim 18 wherein the measuring means measures the magnitude of the T wave characteristic of only intrinsic T waves.

27. The system of claim 18 wherein the predetermined number of cardiac cycles are consecutive cardiac cycles.

28. The system of claim 18 wherein the T wave characteristic is a T wave slope and wherein measuring means includes means for measuring a T wave slope magnitude of each T wave of the predetermined number of cardiac cycles.

29. The system of claim 18 wherein the T wave characteristic is T wave area and wherein the measuring means includes means for measuring T wave area magnitude of each T wave of the predetermined number of cardiac cycles.

30. The system of claim 18 wherein the implantable cardiac device includes a lead system coupled to the sensing means, the lead system having a plurality of T wave sensing electrode configurations, and wherein the system includes selecting means for selecting an electrode configuration from the plurality of T wave sensing electrode configurations that maximizes the measured T wave characteristic.

31. The system of claim 18 further comprising telemetry means for transmitting to an external receiver the presence of a detected T wave alternan pattern.

32. The system of claim 18 further comprising patient alert means for providing an indication, perceptible by the patient, of a detected T wave alternan pattern.

33. The system of claim 18 further comprising memory means for storing at least one of heart rate, time of T wave alternan pattern detection, and patient activity level for the T wave alternan pattern detection.

34. The system of claim 18 further comprising memory means for storing T wave characteristic histogram data.

35. In an implantable cardiac device, a method of detecting a T wave alternan pattern in a patient's heart, the method comprising:
   sensing electrical activity of the patient's heart;
   generating an electrical signal representing electrical activity of the patient's heart;
   computing a metric of a T wave characteristic for each T wave in the electrical signal; and
   processing the measured T wave characteristic metrics for a plurality of T waves to determine whether a T wave alternan pattern exists;
   wherein the detecting step includes the step of determining if a number of measured T wave characteristic magnitudes greater than and less than a T wave characteristic magnitude baseline are substantially equal and each greater than a given number.

36. The method of claim 35 wherein the T wave characteristic baseline is an average of the measured T wave characteristic magnitudes and wherein the method includes the further step of averaging the measured T wave characteristic magnitudes.

37. The method of claim 35 wherein the T wave characteristic baseline is a mean of the measured T wave characteristic magnitudes and wherein the method includes the further step of calculating the mean.

38. The method of claim 35 wherein the given number is one-fourth of the predetermined number.

39. The method of claim 35 including the further step of timing spaced apart times and wherein the generating step is performed at the spaced apart times.

40. The method of claim 35 including the further step of detecting when the patient is at rest and wherein the generating step is performed when the patient is at rest.

41. The method of claim 35 wherein the T wave characteristic is T wave amplitude and wherein the measuring step includes the step of measuring T wave amplitude magnitude of each T wave of the predetermined number of cardiac cycles.

42. The method of claim 35 wherein the implantable cardiac device includes pacing means for providing pacing pulses to the patient's heart during paced cardiac cycles and wherein the measuring step is performed only for T waves occurring during paced cardiac cycles.

43. The method of claim 35 wherein the measuring step is performed on only intrinsic T waves.

44. The method of claim 35 wherein the predetermined number of cardiac cycles are consecutive cardiac cycles.

45. The method of claim 35 wherein the T wave characteristic is a T wave slope and wherein the measuring step includes the step of measuring a T wave slope magnitude of each T wave of the predetermined number of cardiac cycles.

46. The method of claim 35 wherein the T wave characteristic is T wave area and wherein the measuring step includes the step of measuring T wave area magnitude of each T wave of the predetermined number of cardiac cycles.

47. The method of claim 35 wherein the implantable cardiac device includes a lead system having a plurality of T wave sensing electrode configurations, and wherein the method further includes the step of selecting an electrode configuration from the plurality of T wave sensing electrode configurations that maximizes the measured T wave characteristic.

48. The method of claim 35 including the further step of transmitting to an external receiver the presence of a detected T wave alternan pattern.

49. The method of claim 35 including the further step of providing an indication, perceptible by the patient, of a detected T wave alternan pattern.

50. The method of claim 35 including the further step of storing in a memory at least one of heart rate, time of T wave alternan pattern detection, and patient activity level for the T wave alternan pattern detection.

51. The method of claim 35 including the further step of storing in a memory T wave characteristic histogram data.

* * * * *